United States Patent [19]

Ong et al.

[11] Patent Number: 5,006,664
[45] Date of Patent: Apr. 9, 1991

[54] AMINOALKYLTHIODIBENZOTHIEPINS AND RELATED COMPOUNDS

[75] Inventors: Helen H. Ong, Whippany; Vernon B. Anderson, High Bridge, both of N.J.; James A. Profitt, Goshen, Ind.

[73] Assignee: Hoechst-Roussel Pharmaceuticals Inc., Somerville, N.J.

[21] Appl. No.: 453,872

[22] Filed: Dec. 20, 1989

Related U.S. Application Data

[60] Continuation of Ser. No. 14,747, Feb. 13, 1987, abandoned, which is a division of Ser. No. 546,642, Oct. 28, 1983, Pat. No. 4,668,695, which is a continuation-in-part of Ser. No. 174,487, Aug. 1, 1980, abandoned, which is a continuation of Ser. No. 85,751, Oct. 17, 1979, abandoned, which is a continuation-in-part of Ser. No. 860,082, Dec. 13, 1977, abandoned.

[51] Int. Cl.$^5$ .......................................... C07D 337/14
[52] U.S. Cl. ..................................................... 549/12
[58] Field of Search ..................... 549/12, 21; 514/431

[56] References Cited

PUBLICATIONS

March, *Advanced Organic Chemistry*, 2nd Ed., pp. 374–375, 1977, McGraw-Hill Publ.
Ong et al., "Tricyclics . . . [[(Alkylamino)ethyl]thio]-dibenzo[b,f]thiepins", J. Med. Chem., 1982, vol. 25, No. 10, p. 1151.
Seidl et al., "Reaction of Thioxanthylium . . . ", Dept. of Chemistry, Mass. Inst. of Tech., Jun. 1967.
Patai, *The Chemistry of the Thiol Group*, 1974, John Wiley & Sons Publ., pp. 765–767.

*Primary Examiner*—Frederick E. Waddell
*Assistant Examiner*—Catherine S. Kirby Scalzo
*Attorney, Agent, or Firm*—Raymond R. Wittekind

[57] ABSTRACT

Novel aminoalkylthiodibenzothiepins and related compounds, physiologically tolerable acid addition salts thereof, a method of preparing same, pharmaceutical and veterinary preparations including same and methods of treating by administering same are disclosed. These compounds are useful as antidepressant, analgetic, and anticonvulsant agents.

4 Claims, No Drawings

AMINOALKYLTHIODIBENZOTHIEPINS AND RELATED COMPOUNDS

This is a continuation of application Ser. No. 014,747 filed Feb. 13, 1987, now abandoned, which is a division of application Ser. No. 546,642 filed Oct. 28, 1983, now U.S. Pat. No. 4,668,695 which is a continuation-in-part of application Ser. No. 174,487 filed Aug. 1, 1980, now abandoned, which is a continuation of application Ser. No. 085,751, filed Oct. 17, 1979, now abandoned, which is a continuation in-part of application Ser. No. 860,082 filed Dec. 13, 1977, now abandoned.

This invention relates to novel aminoalkylthiodibenzothiepins and related compounds and to their physiologically tolerable acid addition salts which are useful as antidepressant, analgetic and anticonvulsant agents, to methods of treatment with pharmaceutically effective amounts thereof and to pharmaceutical and veterinary compositions containing such a compound as an essential active ingredient.

To the best of our knowledge, the compounds of this invention have not heretofore been described or suggested. Amethoclothepine of the formula

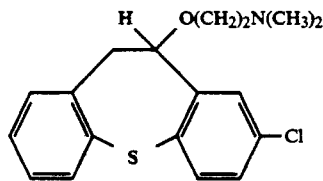

is reported to possess central depressant activity by M. Protvia, et al. II Farmaco XXI 98 (1966).

Japaneses Pat. No. 47-28998 entitled "A Method of Manufacturing Tricyclic Compounds Having an Enolic Ether Bond" pertains to the preparation of compounds depicted by the formula

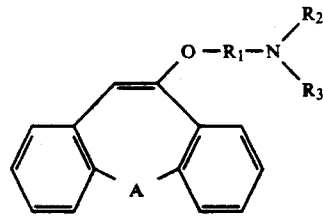

in which A is an alkylimino group, an oxy radical, a thio group or a sulfonyl group, $R_1$ is an alkylene group, $R_2$ and $R_3$ each represent an alkyl group or may be bonded cyclically either through the alkylimine or not through the alkylimine group.

However, the compounds of the present invention possess significant differences with respect to the aforesaid prior art compounds and are not suggested thereby. Furthermore, neither reference suggests the unique methodology required for the preparation of the compounds of the present invention.

The compounds of the present invention conform to the general formula

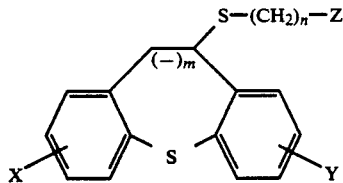

wherein X and Y are the same or different and each can be hydrogen, halogen, trifluoromethyl, loweralkoxy, loweralkyl, loweralkylthio, loweralkylsulfonyl, loweralkylsulfinyl, amino, hydroxy or nitro; Z is halogen or

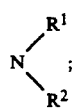

$R^1$ is hydrogen, straight or branched chain loweralkyl, cyano, cycloalkylloweralkyl wherein the cycloalkyl ring contains from 3 to 6 carbon atoms, phenoxycarbonyl of the formula

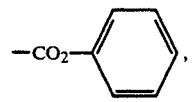

alkoxycarbonyl, loweralkenyl or loweralkynyl; $R^2$ is straight or branched chain loweralkyl or cycloalkylloweralkyl wherein the cycloalkyl ring contains from 3 to 6 carbon atoms; and when $R^1$ and $R^2$ are taken together with the nitrogen atom to which they are attached, the group $R^1-N-R^2$ forms a heterocycle which is morpholino, piperidino, pyrrolidinyl, or N-substituted piperazinyl in which the N-substituent is loweralkyl; m is the integer 0 or 1; and n is an integer of from 2 to 4; and a physiologically tolerable acid addition salt thereof.

In the above definitions, the term "lower" means a group containing up to 6 carbon atoms and the expression "alkylene glycol" refers to a compound formed by replacing 2 non-geminal hydrogen atoms of a straight or branched chain alkyl group of 2 or more carbon atoms by hydroxy groups.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, and oxalic acids.

Compounds of the invention are prepared by one of several methods given below. With the exceptions noted, X, Y, Z, $R^1$, $R^2$, m and n are as defined earlier.

METHOD A

A 10,11-dihydro-10-hydroxydibenzo[b,f]thiepin, of the formula

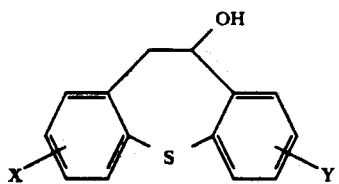

is reacted with aminoalkylthiol of the formula

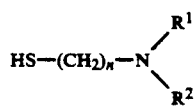

wherein $R^1$ and $R^2$ are the same or different and each can be a straight or branched chain loweralkyl to produce a compound of the invention of the formula

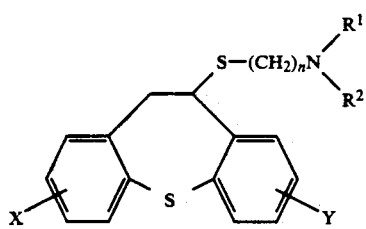

This reaction is carried out with a catalyst/dehydrating agent of boron trifluoride etherate and in the presence of a suitable solvent such as glacial acetic acid at a temperature of about ambient to reflux.

METHOD B

A 10,11-dihydro-10-oxodibenzo[b,f]thiepin, of the formula

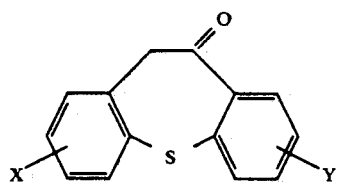

is treated in a manner similar to Method A to obtain a compound of the invention of the formula

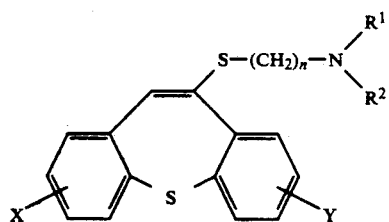

METHOD C

A compound prepared in Method A or B, wherein $R^1$ and $R^2$ are each methyl and n is 2, can be treated with a cyanogen halide such as cyanogen bromide in a suitable solvent and acid scavenger to obtain a mixture of one compound of the invention of the formula

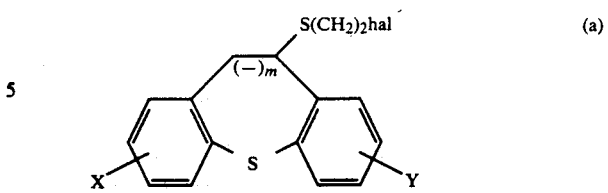

and another compound of the invention of the formula

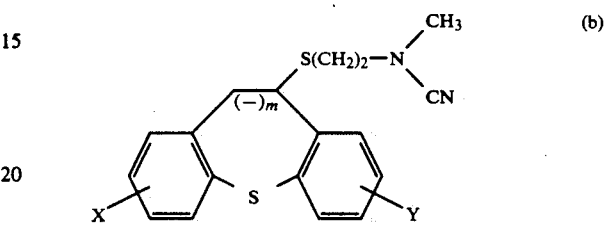

This reaction is carried out at a temperature of from about ambient to reflux. These two compounds of the invention may be isolated and collected by column chromatography.

METHOD D

A compound prepared in Method C of formula (a) can be reacted in a known fashion with a suitable amine to obtain the corresponding compound of the invention of the formula

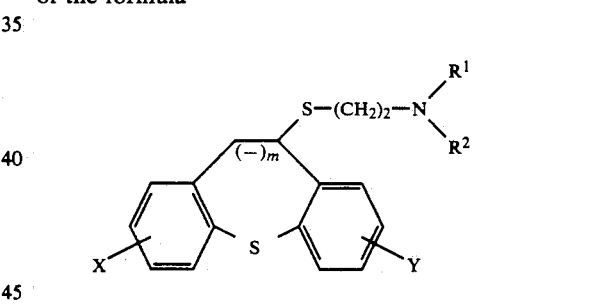

wherein $R^1$ is hydrogen, straight or branched chain loweralkyl, cycloalkylloweralkyl, loweralkenyl or loweralkynyl; $R^2$ is straight or branched chain loweralkyl; and when $R^1$ and $R^2$ are taken together with the nitrogen atom to which they are attached, the group $R^1$-N-$R^2$ forms a heterocycle which is N-substituted piperazinyl, morpholino, piperidino or pyrrolidinyl. A preferred method is carried out with a dimethylformamide solvent, an acid scavenger such as sodium bicarbonate and a reaction initiator such as potassium iodide at a temperature of from ambient to the reflux temperature of the reaction mixture.

METHOD E

A compound prepared in Method A or B can be treated with a chloroformate, e.g. an alkyl or phenyl chloroformate, at a temperature of from 25° to 125° C., in a solvent such as methylene chloride, toluene or benzene to provide the corresponding compound of the invention in which Z is

with $R^1$ being alkoxy or phenoxy carbonyl.

METHOD F

A compound prepared by Method E wherein X and Y are groups as herein before-described other than fluoro is treated with a base such as sodium or potassium hydroxide in a solvent such as water, ethanol or ethylene glycol at a temperature of from ambient to reflux to provide the corresponding compound of the invention in which $R^1$ is hydrogen and X and Y are groups as herein before-described other than fluoro.

When a compound of the formula

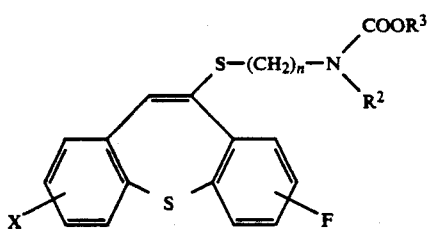

wherein X is hydrogen, bromo, chloro, iodo, trifluoromethyl, loweralkoxy, loweralkyl, loweralkanoyl, loweralkylthio, loweralkylsulfinyl, amino or nitro; $R^2$ is straight or branched chain loweralkyl, loweralkenyl, loweralkynyl or cycloalkylloweralkyl wherein the cycloalkyl ring contains from 3 to 6 carbon atoms; $R^3$ is loweralkyl or phenyl; and n is an integer of from 2 to 4 is treated with an alkali metal or alkaline earth metal hydroxide in an inert solvent in addition to cleavage of the alkoxy- or phenoxycarbonyl groups to the secondary amino function, displacement of the fluoro groups occurs to give a hydroxydibenzo[b,f]thiepin of the formula

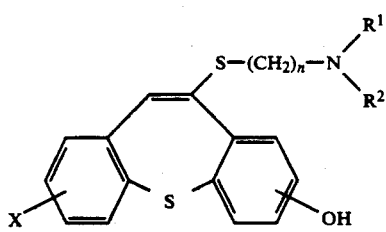

wherein $R^1$ is hydrogen and $R^2$, X and n are as defined above.

The cleavage displacement reaction is conveniently performed in an inert solvent such as an alkylene glycol having 2 to 6 carbon atoms. Suitable alkylene glycols include ethylene glycol, 1,2- and 1,3-propylene glycol, 1,4-, 1,3-, 1,2- and 2,3-butylene glycol, 1,4-, 1,5- and 2,4-pentylene glycol, 1,5-, 1,6- and 2,5-hexylene glycol and the like. Ethylene glycol is preferred.

While the cleavage displacement reaction temperature is not narrowly critical, it is desirable to carry out the reaction at a temperature of from about 100° to 200° C. to assure a reasonable rate of both cleavage and displacement. A reaction temperature of about 160° C. is preferred.

As suitable alkali metal and alkaline earth hydroxides there may be mentioned lithium, sodium and potassium and calcium and barium hydroxides, respectively. Alkali metal hydroxides are preferred, potassium hydroxide being most preferred.

The cleavage displacement reaction is particularly applicable for the preparation of hydroxydibenzo[b,f]-thiepins wherein X is hydrogen, $R^2$ is loweralkyl and n is 2. The reaction is most particularly applicable for the preparation of hydroxydibenzo[b,f]thiepins wherein $R^2$ is methyl and the hydroxy group is attached to the 2-position of the nucleus starting from fluorodibenzo[b,f]thiepines wherein $R^2$ is methyl and the fluoro group is attached to the 2-position of the ring system.

METHOD G

A compound prepared in Method F is treated with a straight or branched chain loweralkyl halide, loweralkynyl halide or cycloalkylloweralkyl halide under conditions normal for such reactions to provide the corresponding compound of the invention in which $R^1$ is straight or branched chain loweralkyl, loweralkenyl, loweralkynyl or cycloalkylloweralkyl. A preferred method is to carry out this substitution in the presence of a solvent such as dimethylformamide, an acid scavenger such as sodium bicarbonate and a reaction initiator such as potassium iodide at the reflux temperature of the solvent.

METHOD H

A compound prepared in any of the above methods, which includes a nitro group can be reduced by a conventional method to produce the corresponding amino compound.

As is appreciated by those skilled in the art, specific reaction conditions in any of the above methods are dependent on and are a function of the ingredients of each procedure.

The compounds of the invention are useful in the treatment of depression in mammals which is evidenced by their ability to inhibit tetrabenazine-induced ptosis in mice [International Journal of Neuropharmacology 8, 73 (1969)], a standard assay for useful antidepressant properties.

Compounds of the invention are further useful as analgesic agents due to their ability to alleviate pain in mammals which is demonstrated in the phenyl-p-quinone writing assay in mice, a standard assay for analgesia [Proc. Soc. Exptl. Biol. Med., 95, 729 (1957)].

Compounds of the present invention are still further useful as anticonvulsant agents for mammals, as evidenced by the method of Woodbury, L.A. and Davenport, V.D. in Arch, Int. Pharmacodynam, Vol. 92, (1952) at pages 97–107.

These compounds are useful, as any of the above three categories of pharmaceutical agents, when administered in an amount ranging from about 0.1 to 100 mg per kg of body weight per day.

Compounds of the present invention are essentially devoid of central nervous system depressant (neuroleptic) activity as determined in the apomorphine induced climbing mice assay, a standard test for central nervous system depressant (neuroleptic) activity described in Example 20.

Compounds of the present invention exhibit a combination of antidepressant activity as determined in the hereinbeforedescribed inhibition of tetrabenazine induced ptosis in mice and analgesic activity as determined in the hereinbeforedescribed phenyl-p-quinone writhing assay in mice and the modified D'Amour-Smith analgesia (tail flick) assay, a standard test for analgesic activity described in Example 21.

Examples of compounds of the invention include:

11-[γ-(dimethylamino)propylthio]-2-ethylsulfonyldibenzo[b, f]thiepin;

11-[β-(bromo)ethylthio]-2-methoxy-10,11-dihydrodibenzo[b,f]thiepin;

2-ethyl-11-[β-(methylamino)ethylthio]dibenzo[b,f]thiepin;

11-[β-(ethylmethylamino)ethylthio]-2-methylsulfinyldibenzo[b,f]thiepin;

11-[β-(ethylmethylamino)ethylthio]-2-methylthiodibenzo[b,f]thiepin;

10,11-dihydro-10-[β-(piperidino) ethylthio]dibenzo[b,f]thiepin;

10,11-dihydro-10-[γ-(N-methylpiperazion)propylthio]dibenzo[b,f]thiepin;

10,11-dihydro-10-[γ-(piperidino)-n-butylthio]dibenzo[b,f]thiepin;

10-[β-(pyrrolidino)ethylthio]dibenzo[b,f]thiepin;

3-chloro-11-[β-(ethylmethylamino)ethylthio]dibenzo[b,f]thiepin;

11-[β-(ethylamino)ethylthio]-10,11-dihydro-4-nitrodibenzo[b,f]thiepin;

11-[β-(ethylamino)ethylthio]-3-trifluoromethyldibenzo[b,f]thiepin;

2-amino-11-[β-(ethylamino)ethylthio]dibenzo[b,f]thiepin;

11-[β-(ethylamino)ethylthio]-3-methoxydibenzo[b,f]thiepin;

11-[β-(diethylamino)ethylthio]-2-n-propyldibenzo[b,f]thiepin;

11-[β-(methylamino)ethylthio]-3-methylthiodibenzo[b,f]thiepin;

8-chloro-10,11-dihydro-10-[β-(dimethylamino)ethylthio]-2-methyldibenzo[b,f]thiepin;

3-fluoro-11-[β-(methylamino)ethylthio]dibenzo[b,f]thiepin;

2-bromo-7-fluoro-11-[β-(dimethylamino)ethylthio]dibenzo[b,f]thiepin;

3-ethyl-11-[β-(methylamino)ethylthio]dibenzo[b,f]thiepin;

11-[β-(ethylamino)ethylthio]-4-nitrodibenzo[b,f]thiepin;

2-methyl-11-[β-(N-methyl-N-methoxycarbonylamino)ethylthio]dibenzo[b,f]thiepin:

10-[β-(N-cyclopropylmethyl-N-methylamino)ethylthio]dibenzo[b,f]thiepin;

10-[β-(N-allyl-N-methylamino)ethylthio]dibenzo[b,f]thiepin; and

10-[β-(N-methyl-N-propargylamino)ethylthio]dibenzo[b,f]thiepin.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coating. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to between 0.5% and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampuls, disposable syringes or multiple dose vials made of glass or plastic.

EXAMPLE 1

Boron trifluoride etherate is added to a solution of 20.0 g of 2-chloro-10,11-dihydro-11-oxodibenzo[b,f]thiepin, 21.8 g of β-dimethylaminoethanethiol hydrochloride and 218 ml of glacial acetic acid. After total addition the reaction mixture is stirred for 30 minutes and then permitted to stand for 48 hours. Thereafter, the mixture is poured into 1200 ml of a 10% sodium hydroxide solution and the basified mixture is extracted with methylene chloride. The combined methylene chloride fractions are successively washed with water, dried and filtered and the filtrate evaporated to dryness leaving a red oil. The oil is column chromatographed through a silica gel/methylene chloride column with a 2-4% methanol in methylene chloride mixture as the eluant. The purified product is converted to its hydrogen chloride salt of 2-chloro-11-[β-(dimethylamino)ethylthio]dibenzo[b,f]thiepin hydrochloride.

Analysis: Calculated for $C_{18}H_{18}ClNS_2 \cdot HCl$: 56.24% C; 4.98% H; 3.64% N. Found: 56.35% C; 5.17% H; 3.47% N.

EXAMPLE 2

A sample of 10,11-dihydro-10-oxodibenzo[b,f]thiepin is treated according to the manipulative procedure of Example 1 to provide 10-[β-(dimethylamino)ethylthio]-dibenzo[b,f]thiepin hydrochloride.

EXAMPLE 3

To a mixture of 1.08 g of β-dimethylaminoethanethiol hydrochloride and 2.5 ml of boron trifluoride etherate is added dropwise a mixture of 1.0 g of 2-chloro-10,11-dihydro-11-hydroxyspirodibenzo[b,f]thiepin in 8 ml of glacial acetic acid. After total addition, the reaction mixture is stirred at ambient temperature for 30 minutes and then permitted to stand for 24 hours. Thereafter, the reaction is poured into 50 ml of a saturated potassium carbonate-ice solution where it is extracted with ether. The combined ether extracts are, successively, washed with a dilute potassium carbonate solution and water and dried, filtered and evaporated. The resulting oil is chromatographed through a silica gel/methylene chloride, a 5% methyl alcohol in methylene chloride eluant and then converted to the maleic acid salt, mp, 99°-101° C. of 2-chloro-10,11-dihydro-11-[β-(dimethylamino)ethylthio]dibenzo[b,f]thiepin maleate.

Analysis: Calculated for $C_{18}H_{20}ClNS_2 \cdot C_4H_4O_4$: 56.70% C; 5.19% H; 3.01% N. Found: 56.70% C; 5.29% H; 3.03% N.

EXAMPLE 4

A sample of 10-[β-(dimethylamino)ethylthio]dibenzo[b,f]thiepin, free base of Example 3, is treated according to the manipulative procedure of Example 3 to provide 10,11-dihydro-10-[β-(dimethylamino)ethylthio]dibenzo[b,f]thiepin hydrochloride.

EXAMPLE 5

A solution of 1.0 g of 2-chloro-11-[β-(dimethylamino)ethylthio]dibenzo[b,f]thiepin free base of Example 1, in 10 ml of methylene chloride is added dropwise to a stirring solution of 0.5 g of cyanogen bromide and 1.0 g of potassium carbonate in 7 ml of methylene chloride. After total addition, the reaction is permitted to stand with complete reaction occuring after about four hours. After the reaction is completed the mixture is filtered and the filtrate evaporated leaving an oil. The oil is chromatographed through a silica gel/methylene chloride column with methylene chloride as the eluant. The desired fraction is evaporated to dryness leaving 2-chloro-11-[β-(N-cyano-N-methyl-)aminoethylthio]dibenzo[b,f]thiepin as a yellow oil Analysis: Calculated for $C_{18}H_{15}ClN_2S_2$: 60.23% C; 4.21% H; 7.81% N. Found: 60.62% C; 4.19% H; 7.75% N.

EXAMPLE 6

To a stirring solution of 0.50 g of phenyl chloroformate and 0.2 g of sodium bicarbonate in 20 ml of methylene chloride is added dropwise a solution of 0.95 g of 2-chloro-11-[β-(dimethylamino)ethylthio]dibenzo[b,f]thiepin, free base of Example 1, in 10 ml of methylene chloride. After total addition the reaction is successively stirred at 25° C. for 24 hours, filtered, diluted with 25 ml of methylene chloride, washed with a 10% sodium hydroxide solution, washed with water, dried and filtered. The filtrate is evaporated leaving a yellow oil which is chromatographed through a silica gel/methylene chloride column with methylene chloride as the eluant. The purified product is the yellow oil of 2-chloro-11-[β-(N-methyl-N-phenoxycarbonylamino)ethylthio]dibenzo[b,f]thiepin.

Analysis: Calculated for $C_{24}H_{20}ClNO_2S_2$: 63.49% C; 4.44% H; 3.09% N. Found: 63.76% C; 4.49% H; 2.90% N.

In a similar fashion a sample of 10-[β-(dimethylamino)ethylthio]dibenzo[b,f]thiepin, free base of Example 2, is treated to provide 10-[β-(N-methyl-N-phenoxycarbonylamino)ethylthio]dibenzo[b,f]thiepin and 11-[β-(dimethylamino)ethylthio]-2-fluorodibenzo[b,f]thiepin, free base of Example 15, is treated to provide 2-fluoro-11-[β-(N-methyl-N-phenoxycarbonylamino)ethylthio]dibenzo[b,f]thiepin.

EXAMPLE 7

A solution of 5.6 g of 2-chloro-11-[β-(N-methyl-N-phenoxycarbonylamino)ethylthio]dibenzo[b,f]thiepin, Example 6, 127 ml of ethylene glycol and 10.8 g of potassium hydroxide is stirred at 150°-155° C. for 30 minutes. Thereafter the reaction mixture is poured onto 300 ml of ice-water and the aqueous mixture is extracted with an ether-toluene (1:1) mixture. The combined extracts, successively, are washed well with water, dried and filtered and the filtrate evaporated leaving an orange oil. The oil is converted to its hydrogen chloride acid salt which is recrystallized from a methanol-acetone-ether mixture to give the product, mp 194°-196° C. of 2-chloro-11-[β-(methylamino)ethylthio]dibenzo[b,f]thiepin hydrochloride.

Analysis: Calculated for $C_{17}H_{16}ClNS_2 \cdot HCl$: 55.13% C; 4.63% H; 3.78% N. Found: 55.28% C; 4.71% H; 3.93% N.

In a similar fashion, 10-[β-(N-methyl-N-phenoxycarbonylamino)ethylthio]dibenzo[b,f]thiepin, hereinabove described, is treated to provide 10-[β-(methylamino)ethylthio]dibenzo[b,f]thiepin hydrochloride.

EXAMPLE 8

A solution of 2-chloro-10,11-dihydro-11-[β-dimethylamino)ethylthio]dibenzo[b,f]thiepin, free base of Example 3, in 10 ml of chloroform is added dropwise to a solution of a stoichiometric amount of cyanogen bromide and an excess amount of potassium carbonate in 5 ml of chloroform. After total addition the reaction mixture is permitted to stand for 10 minutes and then filtered. The filtrate is concentrated to dryness leaving the product 11-(β-bromoethylthio)-2-chloro-10,11-dihydrodibenzo[b,f]thiepin.

In a similar fashion, 11-[β-(dimethylamino)ethylthio]-2-fluorodibenzo[b,f]thiepin, free base of Example 15, is treated to provide 11-(B-bromoethylthio)-2-fluorodibenzo[b,f]thiepin.

EXAMPLE 9

A mixture of stoichiometric amounts of 2-chloro-11-($\beta$-bromoethylthio)-10,11-dihydrodibenzo[b,f]thiepin, Example 8, and N-methylpiperzine, an excess amount of sodium bicarbonate, and 1.0 g of potassium iodide in 15 ml of dimethylformamide is stirred at 80° C. for 16 hours. The mixture is permitted to cool before being diluted with water. The biphasic mixture is extracted thrice with 100 ml portions of ether, the ether extracts are combined and shaken vigorously with a large excess of 2N hydrochloric acid. The acidic solution is basified, liberating the free amine which is extracted into benzene. The benzene solution is dried and the benzene removed under vacuum, leaving the product 2-chloro-10,11-dihydro-11[$\beta$-(4-methylpiperazinyl-l-yl)ethylthio]dibenzo[b,f]thiepin.

In a similar fashion, substituting morpholine for N-methylpiperazine provides 2-chloro-10,11-dihydro-11-($\beta$-morpholinoethylthio)dibenzo[b,f]thiepin.

EXAMPLES 10 AND 11

By following the manipulative procedure of Example 2, respectively substituting $\beta$-diisopropylaminoethanethiol hydrochloride, $\beta$-diethylaminoethanethiol hydrochloride for $\beta$-dimethylaminoethanethiol hydrochloride provides Example 10, 10-[$\beta$-(diisopropylamino)ethylthio]dibenzo[b,f]thiepin hydrochloride and Example 11, 10-[$\beta$-(diethylamino)ethylthio]dibenzo[b,f]thiepin hydrochloride.

EXAMPLE 12 a. A solution of stoichiometric amounts of '2-(4-methylsulfonylphenylthio)benzyl nitrile and 85% potassium hydroxide in an alcohol-water mixture is stirred at 115° C. for 24 hours. Thereafter the reaction mixture is concentrated to an oil. The oil is dissolved in water and the aqueous solution is successively, washed with ether, acidified with dilute hydrochloric acid again providing an oil. This oil is dissolved in methylene chloride and the solution, successively, is dried, filtered and concentrated to dryness leaving the product 2-(4-methylsulfonylphenylthio)phenylacetic acid.

b. A mixture of 1.0 g of 2-(4-methylsulfonylphenylthio)phenylacetic acid and 10 ml of polyphosphoric acid under nitrogen is stirred at 90°-100° C. for 2 hours. The reaction mixture is permitted to cool and then poured into 100 ml of an ice-water slurry. The aqueous solution is basified with 20% sodium hydroxide before being extracted with methylene chloride. The combined extracts are dried and then evaporated to dryness leaving an oil. The oil is chromatographed through a silica gel column with a 2% methanol in methylene chloride eluant. The chromatographed solution is evaporated to dryness providing 10,11-dihydro-2-methylsulfonyl-11-oxodibenzo[b,f]thiepin.

c. A solution of stoichiometric amounts of 10,11-dihydro-2-methylsulfonyl-11-oxodibenzo[b,f]thiepin and dimethylaminoethanethiol hydrochloride and 15 ml of boron trifluoride etherate in 37 ml of glacial acetic acid is stirred until reaction is completed. Thereafter the reaction mixture is poured into 300 ml of a cold sodium hydroxide solution and the resulting solution is extracted with methylene chloride. The combined extracts are washed with water and dried before being filtered. The filtrate is evaporated to dryness leaving an oil which is chromatographed through a silica gel/methylene chloride column with methanol (2–4%) in methylene chloride eluant. The chromatographed solution is evaporated to dryness leaving 11-[($\beta$-dimethylamino)ethylthio]-2-methylsulfonyldibenzo[b,f]thiepin.

EXAMPLE 13

A solution of 2.0 g of 11-($\beta$-bromoethylthio)-2-chloro-10,11-dihydrodibenzo[b,f]thiepin, 1.2 g of potassium iodide and 20 ml of anhydrous dimethylformamide is stirred at 25° C. while methylamine is bubbled in over five minutes. The reaction is stirred at 25° C. for 24 hours, poured into 100 ml of ice water and the resulting product extracted with ether. The ether fractions are combined, washed with water and dried over magnesium sulfate. The dried solution is filtered and evaporated to an oil. Treatment of the oil with ethereal maleic acid provides 2-chloro-10,11-dihydro-11-[$\beta$-(methylamino)ethylthio]dibenzo[b,f]thiepin maleate, mp 110°-112°C. A sample is recrystallized from acetone-ether for elemental analysis: Calculated for $C_{17}H_{18}ClNS_2 \cdot C_4H_4O_4$: 55.80% C; 4.91% H; 3.10% N. Found: 55.91% C; 4.86% H; 2.88% N.

In a similar fashion, 11-($\beta$-bromoethylthio)-2-fluorodibenzo-[b,f]thiepin of Example 8 is treated to provide 11-[$\beta$-(methylamino)ethylthio]-2-fluorodibenzo[b,f]thiepin.

EXAMPLE 14

To a solution of 6.8 g of $\beta$-dimethylaminoethanethiol hydrochloride and 45 ml of glacial acetic aicd, 16 ml of boron trifluoride etherate is added at room temperature with stirring. To the solution is added dropwise 6.0 g of 10,11-dihydro-2-fluoro-11-hydroxyspirodibenzo[b,f]thiepin, dissolved in 50 ml of glacial acetic acid and the reaction mixture is stirred at room temperature for 6 hours and allowed to stand at room temperature for 96 hours. The reaction mixture is poured onto a mixture of 300 ml of saturated potassium carbonate solution and 300 ml of ice. The basic solution is extracted with ether and the ether fractions are combined, washed with dilute potassium carbonate solution, water and dried over anhydrous magnesium sulfate. The solution is filtered, evaporated and the residue chromatographed on a silica gel dichloromethane column with 5–15% methanol/dichloromethane being used for elution to give 2-fluoro-10,11-dihydro-11-[$\beta$-(dimethylamino)ethylthio]dibenzo[b,f]thiepin hydrochloride.

Analysis: Calculated for $C_{18}H_{20}FNS_2 \cdot HCl$: 58.43% C; 5.72% H; 3.79% N. Found: 58.31% C; 5.73% H; 3.80% N.

EXAMPLE 15

To a solution of 5.0 g of 10,11-dihydro-2-fluoro-11-oxodibenzo[b,f]thiepin in 52 ml of glacial acetic acid is added 5.81 g of $\beta$-dimethylaminoethanethiol hydrochloride. After the addition is complete, the mixture is heated to 90° C. whereupon it becomes homogenous. The solution is cooled to 25° C. and 15.4 ml of boron trifluoride etherate is added. After stirring for 3 days at 25° C., an additional 8 ml of boron trifluoride etherate is added and the solution is heated at 60° C. for 5 hours. The reaction mixture is poured into 150 ml of 20% sodium hydroxide solution at 0° C. The mixture is extracted with ether and the combined extracts are washed with 20% sodium hydroxide solution, water, saturated sodium chloride solution, dried over anhydrous magnesium sulfate and filtered. Chromatography of the filtrate on silica gel with 5% methanol/dichloromethane elution provides 2-fluoro-11-[β-(dimethylamino)ethylthio]dibenzo[b,f]thiepin which is converted to its hydrochloride, mp 209°–211° C.

Analysis: Calculated for $C_{18}H_{18}FNS_2 \cdot HCl$: 58.76% C; 5.20% H; 3.81% N. Found: 58.57% C; 5.09% H; 3.53% N.

EXAMPLE 16

Into a mixture of 200 mg of potassium iodide and 35 ml of dry dimethylformamide is bubbled monomethylamine at a fast rate for 5 minutes. A solution of 4.34 g of 11-(β-bromoethyl)-10,11-dihydro-2-fluorodibenzo[b,f]thiepin in 15 ml of dry dimethylformamide is added over 7 minutes while methylamine is bubbled in. Stirring with vigorous bubbling of methylamine is continued for an additional 38 minutes. The reaction is then stoppered and stirred for 3.25 hours. The solution is poured into 350 ml of chilled water and extracted with three 100 ml-portions of ether. The combined ether extract is washed with five 75 ml-portions of water and one 35 ml-portion of saturated sodium chloride solution, dried over anhydrous magnesium sulfate, filtered and evaporated to give 3.60 g of an oil. The oil is dissolved in ether and treated with ethereal maleic acid. Two recrystallizations from acetone-ether give 2-fluoro-10,11-dihydro-10-[(β-methylaminoethyl)thio]dibenzo[b,f]thiepin maleate, mp 114°–116° C.

Analysis: Calculated for $C_{17}H_{18}FNS_2$: 57.93% C; 5.09% H; 3.22% N. Found: 57.62% C; 5.06% H; 3.09% N.

EXAMPLE 17

A mixture of 7.0 g of 2-fluoro-11-[β-(N-methyl-N-phenoxycarbonylamino)ethylthio]dibenzo[b,f]thiepin, 40 g of 85% potassium hydroxide and 150 ml of ethylene glycol is stirred at 160°–170° C. for 2 hours. The cooled mixture is diluted with 300 ml of ice-water and the aqueous solution is acidified with concentrated hydrochloric acid. Basification with ammonium hydroxide (pH 9 ~10) gives a solid which is collected, air-dried and recrystallized from acetone and acetone-hexane to give 2-hydroxy-11-[β-(methylamino)ethylthio]-dibenzo[b,f]thiepin, mp 147°–149° C.

Analysis: Calculated for $C_{17}H_{17}NOS_2$: 64.72% C; 5.43% H; 4.44% N. Found: 64.74% C; 5.59% H; 4.36% N.

EXAMPLE 18

A solution of 4.62 g of cyanogen bromide in 50 ml of chloroform was added dropwise to a solution of 11.5 g of 10,11-dihydro-10-[β-(dimethylamino)ethylthio]-dibenzo[b,f]thiepin in 50 ml of chloroform, with stirring. After stirring at room temperature for 10 min, the solution was evaporated under reduced pressure, and the oily residue was chromatographed over a column of silica gel. Elution with dichloromethane gave 10.8 g (84%) of 10,11-dihydro-10-[β-(bromoethyl)thio]dibenzo-[b,f]thiepin, mp 60°–62° C.

Analysis: Calculated for $C_{16}H_{15}BrS_2$: 54.70% C; 4.30% H. Found: 54.89% C; 4.24% H.

EXAMPLE 19

Into a solution of 10,11-dihydro-10-[β-bromoethyl)-thio]dibenzo[b, f]thiepin in 10 ml of anhydrous dimethylformamide containing a few crystals of potassium iodide was bubbled gaseous monomethylamine for 30 min. The saturated solution was stoppered and allowed to stand at room temperature for 16 hrs. The mixture was diluted with water. The organic materials were extracted into ether and the combined ether solution was washed four times with water. After drying, the ethereal solution was treated with anhydrous hydrochloric acid to give a precipitate. Trituration with methanol gave 2.2 g (65.3%) of 10,11-dihydro-10-[-(methylamino)ethylthio]dibenzo[b,f]thiepin hydrochloride, mp 117°–119° C.

Analysis: Calculated for $C_{17}H_{19}NS_2 \cdot HCl$: 60.42% C; 5.97% H; 4.15% N. Found: 60.20% C; 5.91% H; 4.15% N.

EXAMPLE 20

Central Nervous System Depressant (Neuroleptic) Activity Climbing Mice Assay Method The subject CD-1 male mice (23–27 grams) were group-housed under standard laboratory conditions. The mice were individually placed in wire mesh stick cages (4"×4"×10") and were allowed one hour for adaptation and exploration of the new environment. Then apomorphine was injected subcutaneously at 1.5 mg/kg, a dose causing climbing in all subjects in 30 minutes. Compounds to be tested for neuroleptic activity were injected intraperitoneally 30 minutes prior to the apomorphine challenge at a screening dose of 10 mg/kg.

For evaluation of climbing, 3 readings were taken at 10, 20 and 30 minutes after apomorphine administration according to the following scale:

| Climbing Behavior | Score |
| --- | --- |
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine were discarded.

With full-developed apomorphine climbing, the animals were hanging onto the cage walls, rather motionless, over longer periods of time. By contrast, climbs due to mere motor stimulation usually only lasted a few seconds.

The climbing scores were individually totaled (maximal score: 6 per mouse over 3 readings) and the total score of the control group (vehicle intraperitoneally—apomorphine subcutaneously) was set to 100%. $ED_{50}$ values with 95% confidence limits were calculated by a Linear Regression Analysis.

| | Results: | |
| --- | --- | --- |
| Compound | Dose (mg/kg) | Activity (% Climbing Score) |
| 2-chloro-11-[β-(dimethylamino)ethylthio]dibenz[b,f]thiepin | 10 | −5 |
| 10-[β-(dimethylamino)-ethylthio]dibenz[b,f]thiepin | 10 | +5 |

References:
Protais, P., Costentin, J. and Schwartz, J.: Climbing behavior induced by apomorphine in mice: A simple test for the study of dopamine receptors in striatum. Psychopharmacol., 50: 1-6, 1976.
Costall, B., Naylor, R. J. and Nohria, V.: Climbing behavior induced by apomorphine in mice: A potent model for the direction of neuroleptic activity. Eur. J. Pharmacol., 50: 39-50, 1978.

EXAMPLE 21

Analgesic Activity Modified D'Amour-Smith Assay (Tail Flick)

Method

Male mice (Charles River: CD-1) from 18–30 grams were used as test subjects. The mouse tails were individually placed on a "Vee" block and, subsequently, a painful stimulus was produced by an intense light beam (Emdie Instrument Co., Louisa, Va.). The subject quickly responds to the noxious stimuli by flicking its tail. The reaction time, the interval between stimulus onset and response, was automatically measured in 1/10-second increments. Prior to drug administration, two control readings of reaction time were measured for each subject with approximately 15 minutes separating the tests. Subjects were discarded if their reaction times in these control tests varied by more than one second or if their inclusion in the study group caused the spread of reaction times to exceed three seconds.

The mean response time ($\bar{x}$) and the standard deviation (SD) of the values were then calculated for each set of control scores. The formula presented below was used to calculate cut-off values (C.O.) for each set of control scores and the average of these C.O. values was used to determine evidence of analgesic activity in subsequent drug testing.

$$\bar{x} + SD\,(2) = C.O.$$

$\bar{x}$ = Mean control response times for group
SD = Standard deviation of the response times The C.O. value was actually a determination of a reaction time which exceeds the mean by two standard deviations. Any reaction time, in subsequent drug tests, which was greater than the C.O. value, therefore exceeds 95% of a normal Gaussian distribution and was called a "positive response" indicative of analgesic activity. Latency changes were calculated by substracting the tail flick latency of the average control times from the latency after treatment for each mouse.

Compounds were tested in treatment groups of ten subjects and drugs, prepared in distilled water, were generally administered subcutaneously (s.c.) in volumes equivalent to 10 cc/kg. The initial testing was usually in the form of a time response at intervals of 15, 30, 45 and 60 minutes after dosing. If analgesic activity was still increasing at 60 minutes, then two additional groups were tested at 90 minute and 120 minute post dosing.

A time response indicated the period of greatest analgesic effect after dosing. Percent analgesic activity was calculated in the following manner:

$$\frac{\%\ \text{Positive for Drug Grp.} - \%\ \text{Positive for Veh. Control Grp.} \times 100}{100 - \%\ \text{Positive for Vehicle Control Group}}$$

The ED$_{50}$ was determined at the peak time of drug activity. A minimum of three dose groups were employed. Drugs were administered in a randomized manner. ED$_{50}$'s were calculated using Litchfield-Wilcoxon (LITWL on PDP II) computer analysis.

| Compound | Results: Dose (mg/kg) | Analgesic Activity (%) |
|---|---|---|
| 10-[β-dimethylamino)-ethylthio]dibenz[b,f]thiepin | 25 | 20 |
| 2-chloro-11-[β-(dimethylamino)ethylthio]dibenz[b,f]thiepin | 14.3 | 50 |

Reference:
(1) D'Amour, Fred and Smith, Donn. J. Pharmacol. Exptl. Therap. 72: 74–79 (1941).
Grp. = Group
Veh. = Vehicle

We claim:

1. A method for preparing a compound of the formula

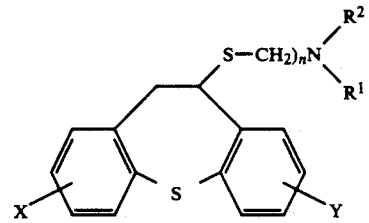

in which X and Y are the same or different and each can be hydrogen, halogen, trifluoromethyl, loweralkoxy, loweralkythio, loweralkylsulfonyl, loweralkylsulfinyl, amino, hydroxy or nitro; $R^1$ and $R^2$ are the same or different and each can be straight or branched chain loweralkyl; and n is an integer of from 2 to 4 which comprises reacting a 10,11-dihydro-10-hydroxydibenz[b,f]thiepin of the formula

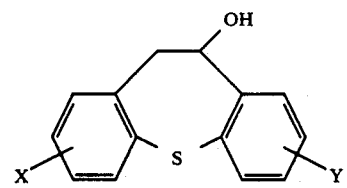

with an aminoalkylthiol of the formula

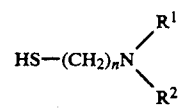

in the presence of boron trifluoride etherate and a solvent at a temperature of from about ambient to reflux.

2. The process of claim 1 in which the solvent is glacial acetic acid.

3. A process for preparing a compound of the formula

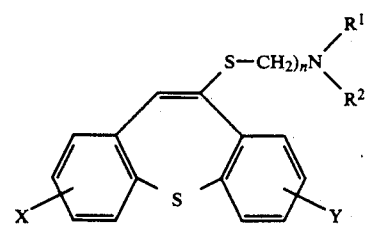

in which X and Y are the same or different, and each can be hydrogen, halogen, trifluoromethyl, loweralkoxy, loweralkylthio, loweralkylsulfonyl, loweralkylsulfinyl, nitro or amino; $R^1$ and $R^2$ are the same or different and each can be straight or branched chain loweralkyl; and n is an integer of from 2 to 4 which comprises reacting a 10,11-dihydro-10-oxodibenzo[b,f]thiepin of the formula

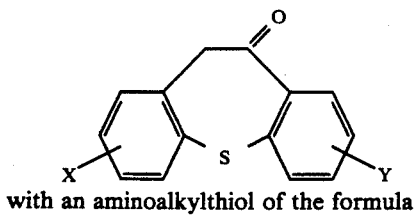

with an aminoalkylthiol of the formula

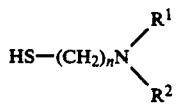

in the presence of boron trifluoride etherate and a solvent at a temperature of from about ambient to reflux.

4. The process according to claim 3 in which the solvent is glacial acetic acid.

* * * * *